United States Patent [19]

Palameta et al.

[11] 4,382,088
[45] May 3, 1983

[54] 4,7-DIHYDRO-4,7-DIOXI-1H-CYCLOHEPTA[B]PYRIDINE DERIVATIVES

[75] Inventors: Bozidar Palameta, Dollard des Ormeaux; Tibor Bogri, St. Laurent; Jehan Bagli, Kirkland, all of Canada

[73] Assignee: Ayerst, McKenna & Harrison, Inc., Montreal, Canada

[21] Appl. No.: 295,180

[22] Filed: Aug. 21, 1981

[51] Int. Cl.³ .................. C07D 221/04; A61K 31/435
[52] U.S. Cl. .................. 424/256; 546/183; 560/125
[58] Field of Search ............... 424/256; 546/183

[56] References Cited

U.S. PATENT DOCUMENTS 3,821,383  6/1974  Sestanj et al. .................. 424/258
4,130,649  12/1978  Bagli .................. 424/266

OTHER PUBLICATIONS

Hayman, J. Biol. Chem. 240, 877 (1965).
D. Dvornik et al., Science, 182, 1146 (1973).
M. J. Peterson et al., Metabolism, 28, (Suppl. 1), 456 (1979).
R. Slack and C. F. Attridge, Chemistry and Industry, 471 (1952).
K. Yamane, Chem. Abstr., 56, 4486 (1962) for Nippon Kagaku Zasshi, 81, 295 (1960).

*Primary Examiner*—Mark L. Berch
*Attorney, Agent, or Firm*—Arthur E. Wilfond

[57] ABSTRACT

Aldose reductase inhibitors of the formula

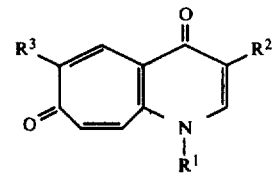

in which $R^1$ is $CH_2COOR^4$ wherein $R^4$ is hydrogen or lower alkyl; $R^2$ is $COOR^5$ wherein $R^5$ is hydrogen or lower alkyl; and $R^3$ is lower alkoxy, benzyloxy or $CH_2COOR^6$ wherein $R^6$ is hydrogen or lower alkyl; with the provisos that when $R^4$ is hydrogen then $R^5$ and $R^6$ is hydrogen; and that when $R^4$ is lower alkyl then $R^5$ and $R^6$ are lower alkyl with $R^4$ and $R^6$ being the same lower alkyl; are useful for treating diabetic complications.

11 Claims, No Drawings

4,7-DIHYDRO-4,7-DIOXI-1H-CYCLOHEPTA[B-]PYRIDINE DERIVATIVES

RELATED APPLICATION

Related hereto is U.S. Patent Application Ser. No. 295,179, filed on the same date as this application.

This application relates to cyclohepta[b]pyridine derivatives. More specifically, this application relates to 4,7-dihydro-4,7-dioxo-1H-cyclohepta[b]pyridine-1-acetic acid derivatives and therapeutically acceptable salts thereof, to a process for their preparation, to pharmaceutical compositions thereof, and to methods for using the derivatives. The derivatives have pharmacologic properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts, and atherosclerosis. These complications have been linked to the undesirable accumulation of sorbitol in diabetic tissue, which in turn result from the high levels of glucose characteristic of the diabetic patient.

In mammals, including humans, the key enzyme involved in the conversion of hexoses to polyols (the sorbitol pathway) is aldose reductase. J. H. Kinoshita and collaborators, see J. H. Kinoshita, et al., Biochem. Biophys. Acta., 158, 472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. R. Baker, Diabetol., 6, 531 (1970).

1,3-Dioxo-1H-benz[de]isoquinoline-2(3H)-acetic acid has been reported to be an effective inhibitor of aldose reductase, see D. Dvornik et al., Science, 182, 1146 (1973), and to be useful for the treatment of diabetic complications such as diabetic cataracts, neuropathy, nephropathy and retinopathy, see K. Sestanj, N. Simard-Duquesne and D. M. Dvornik, U.S. Pat. No. 3,821,383, June 28, 1974. (S)-6-Fluoro-2,3-dihydrospiro(4H-1-benzopyran-4,4′-imidazolidine)-2′,5′-dione (sorbinil) is still another compound that has received attention because of its aldose reductase inhibiting properties, see M. J. Peterson et al., Metabolism, 28 (Suppl. 1), 456 (1979). Accordingly, these compounds represent an important new approach for the treatment of diabetes mellitus.

The present application discloses novel cyclohepta[b]pyridine derivatives, which are effective inhibitors of aldose reductase. Furthermore, these new derivatives are structurally quite different from the above noted aldose reductase inhibitors. Related prior art compounds, on a structural basis, are a group of cyclohepta[b]pyridine-2-carboxylic acid derivatives, reported by J. F. Bagli and T. Bogri in U.S. Pat. No. 4,130,649, issued Dec. 19, 1978. Another group of related compounds are 4,6-dihydroxy-7-oxo-7H-cyclohepta[b]pyridine-3-carboxylic acid derivatives reported by R. Slack and C. F. Attridge, Chemistry and Industry, 471 (1952) and by K. Yamane, see Chem. Abstr., 56, 448b (1962) for Nippon Kagaku Zasshi, 81, 295 (1960). The prior art compounds are distinquished from the present compounds by the nature of the substituents on the cyclohepta[b]pyridine ring system and by different pharmacologic properties.

SUMMARY OF THE INVENTION

The cyclohepta[b]pyridine derivatives of this invention are represented by formula I

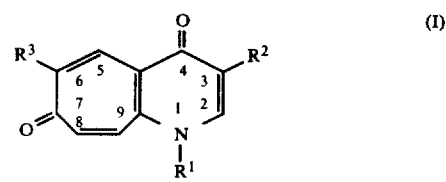

in which $R^1$ is $CH_2COOR^4$ wherein $R^4$ is hydrogen or lower alkyl; $R^2$ is $COOR^5$ wherein $R^5$ is hydrogen or lower alkyl; and $R^3$ is lower alkoxy, benzyloxy or $OCH_2COOR^6$ wherein $R^6$ is hydrogen or lower alkyl; with the provisos that when $R^4$ is hydrogen then $R^5$ and $R^6$ are hydrogen, and that when $R^4$ is lower alkyl then $R^5$ and $R^6$ are lower alkyl with $R^4$ and $R^6$ being the same lower alkyl; or a therapeutically acceptable salt, with an organic or inorganic base, of the compound of formula I having carboxyls.

A preferred group of derivatives is represented by the compound of formula I in which $R^1$ is $CH_2COOR^4$ wherein $R^4$ is hydrogen, methyl or ethyl; $R^2$ is $COOR^5$ wherein $R^5$ is hydrogen, methyl or ethyl; and $R^3$ is methoxy, benzyloxy or $OCH_2COOR^6$ wherein $R^6$ is hydrogen, methyl or ethyl.

Another preferred group of the derivatives is represented by the compound of formula I in which $R^1$ is $CH_2COOH$, $R^2$ is COOH and $R^3$ is methoxy, benzyloxy or $OCH_2COOH$.

The compounds of formula I can be prepared by a process described hereinafter.

A method is provided for preventing or relieving diabetes mellitus associated complications in a diabetic mammal by administering to said mammal a prophylactic or alleviating amount of the compound of formula I or therapeutically acceptable salt thereof with an organic or inorganic base. These complications include neuropathy, nephropathy, retinopathy and cataracts.

The compounds of formula I, or a therapeutically acceptable salt thereof with an organic or inorganic base, when admixed with a pharmaceutically acceptable carrier, form a pharmaceutical composition which can be used according to the preceding method.

DETAILED DESCRIPTION OF THE INVENTION

The term "lower alkyl" as used herein means a straight chain alkyl radical containing from one to six carbon atoms, preferably one to two carbon atoms, or a branched chain alkyl radical containing three to four carbon atoms and includes methyl, ethyl, propyl, 1- methylethyl, propyl, 2-methylpropyl and 1,1-dimethylethyl.

The term "lower alkoxy" as used herein means a straight chain alkoxy radical containing from one to six carbon atoms, preferably one to two carbon atoms, or a branched chain alkoxy radical containing three to four carbon atoms, and includes methoxy, ethoxy, 1-methylethoxy, butoxy and hexanoxy.

The term "halo" as used herein means a halo radical and includes fluoro, chloro, bromo and iodo.

The term "lower alkanol" as used herein means both straight and branched chain alkanols containing from one to four carbon atoms and includes methanol, ethanol, isopropanol, butanol and the like.

The term "inorganic proton acceptor" as used herein means the inorganic bases, preferably the alkali metal hydrides, hydroxides and carbonates, or their corresponding lower alkoxides, for example, sodium hydride, potassium hydroxides, sodium carbonate, potassium carbonate, sodium ethoxide and the like.

The term "organic proton acceptor" as used herein means the organic bases or amines, for instance, triethylamine, pyridine, N-ethylmorpholine, 1,5-diazabicyclo[4.3.0]non-5-ene and the like.

The term "proton acceptor" as used herein means a proton acceptor selected from an organic proton acceptor and inorganic proton acceptor, as defined hereinabove.

The compounds of formula I having carboxyls, i.e. compounds of formula I in which $R^1$ is $CH_2COOH$ and $R^2$ is COOH, and optionally $R^3$ is $OCH_2$—COOH, form salts with suitable therapeutically acceptable inorganic and organic bases. These derived salts possess the same activity as their parent acid and are included within the scope of this invention. The acid is transformed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltriethanol and trimethyl-monoethanol) and cyclic ammonium salts, for example the N-methyl-pyridinium, N-methyl-N-(2-hydroxyethyl)-morpholinium N,N-dimethylmorpholinium, N-methyl-N-(2-hydroxyethyl)-morpholinium, N,N-dimethyl-piperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula I is dissolved in a suitable solvent of either moderate or low polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

The compounds of this invention and their addition salts with pharmaceutically acceptable organic or inorganic bases may be administered to mammals, for example, man, cattle or rabbits, either alone or in dosage forms, i.e., capsules or tablets, combined with pharmacologically acceptable excipients, see below. Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the present therapeutic agents will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects. For topical administration a 0.05–0.2% solution may be administered dropwise to the eye. The frequency of instillation varies with the subject under treatment from a drop every two or three days to once daily. For oral or parenteral administration a preferred level of dosage ranges from about 50 mg to about 250 mg per kilo of body weight per day, although aforementioned variations will occur. However, a dosage level that is in the range of from about 100 mg to about 250 mg per kilo of body weight per day is most satisfactory.

Unit dosage forms such as capsules, tablets, pills and the like may contain from about 25 mg to about 500 mg of the active ingredients of this invention, dependent on the type of unit dosage, optionally with a quantity of a pharmaceuticaly carrier. Thus, for oral administration, capsules can contain from between about 25 mg to about 500 mg of the active ingredients of this invention with or without a pharmaceutical diluent. Tablets, either effervescent or noneffervescent, can contain between about 25 to 500 mg of the active ingredients of this invention together with conventional pharmaceutical carriers. Thus, tablets which may be coated and either effervescent or noneffervescent may be prepared according to the known art. Inert diluents or carriers, for example, magnesium carbonate or lactose, can be used together with conventional disintegrating agents for example, magnesium stearate.

Syrups or elixirs suitable for oral administration can be prepared from water soluble salts, and may advantageously contain glycerol and ethyl alcohol as solvents or preservatives.

The compounds of formula I, or their therapeutically acceptable salts, also can be used in combination with insulin or oral hypoglycemic agents to produce beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds of formula I, or their therapeutically acceptable salts, can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 34 ed., Medical Economics Co., Oradell, N.J., U.S.A., 1980. When used in combination, the compounds of formula I, or their therapeutically acceptable salts, are administered as described previously. The compounds of formula I, or their therapeutically acceptable salt, can be administered with the oral hypoglycemic agent in the form of a pharmaceutical composition comprising effective amounts of each agent.

The aldose reductase inhibiting effects of the compounds of formula I and their pharmaceutically acceptable salts with organic or inorganic bases can be demonstrated by employing an in vitro testing procedure similar to that described by S. Hayman and J. H. Kinoshita, J. Biol. Chem., 240, 877 (1965). In the present case the procedure of Hayman and Kinoshita is modified in that the final chromatography step is omitted in the preparation of the enzyme from bovine lens.

The following results were obtained when the foregoing listed compounds of formula I were evaluated in the above in vitro test.

| Compound of Formula I | | | Example In Which Compound | % Inhibition at Different Molar Concentrations (in vitro) | | |
|---|---|---|---|---|---|---|
| $R^1$ | $R^2$ | $R^3$ | Is Prepared | $10^{-5}$ | $10^{-6}$ | $10^{-7}$ |
| $CH_2COOC_2H_5$ | $COOC_2H_5$ | $OCH_2COOC_2H_5$ | 5 | 40 | | |
| $CH_2COOH$ | $COOH$ | $OCH_3$ | 7 | 89 | 79 | 30 |
| $CH_2COOH$ | $COOH$ | $OCH_2COOH$ | 7 | 97 | 88 | 31 |
| $CH_2COOH$ | $COOH$ | $OCH_2C_6H_5$ | 8 | 88 | 79 | 37 |

The aldose reductase inhibiting property of the compound of this invention and its utilization in preventing, diminishing and alleviating diabetic complications also are demonstrable in experiments using galactosaemic rats, see Dvornik et al., cited above.

PROCESS

The compounds of formula I can be prepared by a process illustrated by the following scheme.

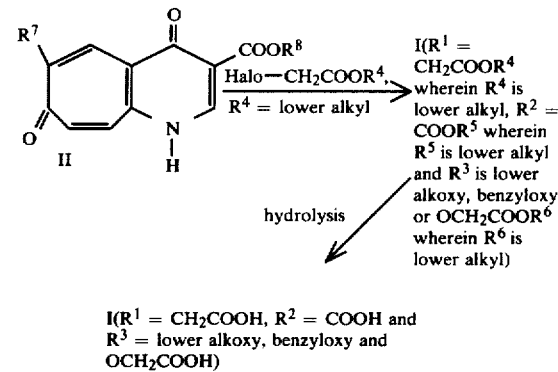

$(R^1 = CH_2COOH, R^2 = COOH$ and $R^3 = $ lower alkoxy, benzyloxy and $OCH_2COOH)$ The process comprises condensing a compound of formula II, in which $R^7$ is lower alkoxy, benzyloxy or hydroxy and $R^8$ is lower alkyl, with a haloacetic acid lower alkyl ester in the presence of a proton acceptor to obtain the corresponding compound of formula I in which $R^1$ is $CH_2COOR^4$ wherein $R^4$ is lower alkyl, $R^2$ is $COOR^5$ wherein $R^5$ is lower alkyl and $R^3$ is lower alkoxy, benzyloxy or $OCH_2COOR^6$ wherein $R^6$ is lower alkyl; (b) and, if required, hydrolyzing the last named compound of formula I to obtain the corresponding compound of formula I in which $R^1$ is $CH_2COOH$, $R^2$ is $COOH$ and $R^3$ is lower alkoxy, benzyloxy or $OCH_2COOH$; (c) and when a therapeutically acceptable salt, with an organic or inorganic base, of the compound of claim 1 having at least one carboxy is required, neutralizing the corresponding compound of formula I with a therapeutically acceptable organic or inorganic base.

The compound of formula II, which serves as a starting material for the above process, can be prepared by the process illustrated as follows:

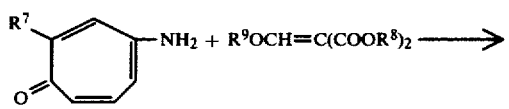

III

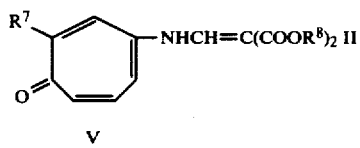

V wherein $R^7$ is lower alkoxy, benzyloxy or hydroxy, and $R^8$ and $R^9$ are lower alkyl.

The aminotropones or aminotropolones of formula III are known, for example see T. Nozoe et al., Proc. Japan Acad., 27, 188 (1951), or they can be prepared by known methods.

With reference to the latter reaction scheme, the aminotropone or aminotropolone of formula III in which $R^7$ is as defined herein is condensed with a (lower)alkoxymethylenemalonic acid di(lower)alkyl ester of formula IV in which $R^8$ and $R^9$ are lower alkyl in the presence of an alkali metal lower alkoxide to obtain the corresponding diester of formula V in which $R^7$ and $R^8$ are as defined herein. This condensation can be accomplished conveniently by heating a mixture of the aminotropolone with an excess (preferably five to ten molar equivalents) of the (lower)alkoxymethylenemalonic acid di(lower)alkyl ester at temperatures ranging from 120° to 160° C., preferably 135°–145° C. An inert high boiling solvent can be used for this reaction; however, an excess of the (lower)alkoxymethylenemalonic acid di(lower)alkyl ester is the most practical solvent. The reaction is maintained at the elevated temperature for about one to four hours. Thereafter, the reaction mixture is cooled and the desired diester of formula V is separated from the excess (lower)alkoxymethylenemalonic acid di(lower)alkyl ester by standard laboratory means, for instance chromatography. Often, the diester of formula V crystallizes at this point and can be separated by filtration.

Thereafter, the diester of formula V is cyclized at an elevated temperature to give the cycloheptapyridine compound of formula II. Although the temperature and reaction time will vary depending on the particular nature of the diester of formula V, it has been found that the cyclization proceeds quite readily at elevated temperatures ranging from 240° to 280° C. Care should be taken to avoid prolonged heating of the reaction mixture which will cause decomposition of the desired product. In most cases, the cyclization is effected at the preceding elevated temperature within ten to 30 minutes. The cyclization is most conveniently done in an inert high boiling solvent. Diphenyl ether (bp 256° C.) and mixtures of diphenyl ether and diphenylmethane are suitable solvents for this purpose.

In the next step, the cycloheptapyridine compound of formula II is condensed with a haloacetic acid lower alkyl ester in the presence of a proton acceptor to give the ester compound of formula I in which $R^1$ is $CH_2COOR^4$ wherein $R^4$ is lower alkyl, $R^2$ is $COOR^5$ wherein $R^5$ is lower alkyl and $R^3$ is lower alkoxy, benzyloxy or $OCH_2COOR^6$ wherein $R^6$ is lower alkyl.

Practical and convenient conditions for effecting the latter condensation include the use of one to two molar equivalents of the proton acceptor. Inorganic proton acceptors, for example, sodium hydride, sodium hydroxide or potassium carbonate, have been found to be suitable proton acceptors. Any solvent, which does not interfer with the reaction, can serve as the reaction medium. Suitable solvents include dimethylformamide, dimethyl sulfoxide, toluene, acetone and tetrahydrofuran. Preferred conditions for effecting the condensation include the use of sodium hydride or potassium carbonate as the proton acceptor and dimethylformamide as the solvent. Although the optimum temperature and reaction time will vary depending on the reactants employed, the reaction is performed generally at 20° to 120° C., or the boiling point of the reaction mixture, for a period of 30 minutes to 48 hours.

Finally, when the compound of formula I in which $R^1$ is $CH_2COOH$, $R^2$ is $COOH$ and $R^3$ is lower alkoxy, benzoyloxy or $OCH_2COOH$ is required, hydrolysis of the corresponding ester compound of formula I in which $R^1$ is $CH_2COOR^4$ wherein $R^4$ is lower alkyl, $R^2$ is $COOR^5$ wherein $R^5$ is lower alkyl and $R^3$ is lower alkoxy, benzyloxy or $OCH_2COOR^6$ wherein $R^6$ is lower alkyl gives the desired compound. The hydrolysis can be performed most conveniently by employing a base in the presence of sufficient water, followed by acidification of the reaction mixture to yield the desired acid. However, it should be understood that the manner of hydrolysis for the process of this invention is not intended to be limited to basic hydrolysis since hydrolysis under acidic conditions and other variations, for example treatment with lithium iodide in collidine (see L. F. Fieser and M. Fieser, "Reagents for Organic Synthesis", John Wiley and Sons, Inc., New York, 1969, pp. 615–617), also are applicable. Hydrolysis under acidic conditions is preferred for tert butyl esters.

For acid hydrolysis, a preferred embodiment involves subjecting the corresponding ester to the action of a strong organic or inorganic acid, for example, hydrochloric acid, sulfuric acid, trifluoroacetic acid or p-toluenesulfonic acid, in the presence of sufficient water to effect hydrolysis. Suitable solvents include water, the lower alkanols and acetic acid. The reaction mixture is maintained at a temperature ranging from 20° to 100° C. or at the reflux temperature of the solvent employed until hydrolysis is complete. Usually a reaction time of 30 minutes to two hours is sufficient.

For basic hydrolysis, a preferred embodiment involves subjecting the ester to the action of a strong base, for example, sodium hydroxide or potassium hydroxide, in the presence of sufficient water to effect hydrolysis of the ester. The hydrolysis is performed using a suitable solvent, for example, methanol, ethanol or 2-methoxyethanol. The reaction mixture is maintained at a temperature ranging from 25° to 100° C. or at the reflux temperature of the solvent employed until hydrolysis is complete. Usually from 10 minutes to 6 hours is sufficient. The reaction mixture is then rendered acidic with an acid, for example, acetic acid, hydrochloric acid or sulfuric acid, to release the free acid.

Optionally, if the therapeutically acceptable salt, with an inorganic base, of the compound of formula I is desired, the basic hydrolysis can be effected with a strong base having a physiologically compatible cation, for example $Na^+$, $K^+$ or $Ca^{++}$. In this instance, a sufficient amount of the base is used to give the desired salt and the salt is isolated by evaporating the solvent from the reaction mixture.

The following examples further illustrate this invention.

EXAMPLE 1a

5-Amino-2-methoxy-2,4,6-cycloheptatrien-1-one Hydrochloride (III; $R^7$=OCH$_3$)

5-Acetamido-2-methoxy-2,4,6-cycloheptatrien-1-one (17 g), described by T. Nozoe et al., Proc. Japan Acad., 27, 188 (1951), was suspended in a solution of 18.25 g of anhydrous HCl dissolved in 250 ml of methanol. The suspension was stirred at 25° C. After one hr, a complete solution resulted. After an additional ½ hr, a precipitate had occurred. The precipitate was collected by filtration giving 8.2 g of the title compound; mp 198° C. (dec); nmr (DMSO-d$_6$) δ4.0 (s, 3h), 7.15 (broad, s, 3H), 7.45 (t, 2H), 7.90 (t, 2H); uv λmax (EtOH) 365 nm ($\epsilon$18,335), 355 (16,075) and 234 (23,360). The filtrate was concentrated yielding another 8.1 g of the title compound.

EXAMPLE 1b

5-Amino-2-benzyloxy-2,4,6-cycloheptatrien-1-one (III; $R^7$=OCH$_2$C$_6$H$_5$)

A solution of 5-amino-2-hydroxy-2,4,6-cycloheptatrien-1-one (120 g), described by T. Nozoe et al., Proc. Japan Acad., 27, 188 (1951), in acetic anhydride (750 ml) was heated at 100° C. for 5 hr. On cooling the reaction mixture, 2-acetoxy-5-acetylamino-2,4,6-cycloheptatrien-1-one (116.45 g) crystallized out of solution and was collected by filtration. The filtrate was concentrated and diluted with ethyl acetate whereby another 25.9 g of product, suitable for the next step, was obtained.

A suspension of 2-acetoxy-5-acetylamino-2,4,6-cycloheptatrien-1-one (40 g) in 180 ml of water was heated at reflux for 2 hr. The resulting clear solution was filtered, while still hot, and then cooled to 25° C. 5-Acetylamino-2-hydroxy-2,4,6-cycloheptatrien-1-one (31.8 g) precipitated out of solution.

A mixture of the latter product (36 g), benzyl chloride (100 g), sodium hydride (5 g, 50% suspension in mineral oil) and dimethylformamide (DMF, 1.5 l) was heated with stirring at 140° C. for 4 hr. The mixture was concentrated by evaporation under reduced pressure. The residue was purified by chromatography on silica gel using chloroform-methanol (97:3) as eluant. After elution of a small amount of the O,N-dibenzyl by-product, the pure product (7.5 g) was obtained. Continued elution gave fractions which were a mixture of the product and the starting material. The latter fractions were combined and diluted with excess 1 N aqueous NaOH. The basic solution was extracted with chloroform to give 6.0 g of the pure product. The pure product, 5-acetylamino-2-benzyloxy-2,4,6-cycloheptatrien-1-one had nmr (CDCl$_3$) δ2.05 (s, 3H), 5.1 (s, 2H), 7.29 (m, 9H), 8.65 (s, 1H).

The latter compound (12.6 g) was suspended in a solution of anhydrous hydrogen chloride (18 g) in methanol (250 ml). After stirring at 25° C. for 24 hr, the reaction mixture became homogeneous. Concentrated ammonia was carefully added to the reaction mixture until a pH of about 8 was obtained. The precipitated ammonium chloride was collected by filtration. The filtrate was evaporated to a small volume. Additional ammonium chloride precipitated out and was removed by filtration. The filtrate was diluted with chloroform to give 10 g of the title compound as a precipitate; nmr (DMSO-d$_6$) δ4.95 (s, 2H), 6.05 (s, 1H), 6.3 (s, 2H), 6.95 (m, 3H), 7.3 (m, 5H); ir (Nujol*) 3340, 3180, 1500 cm$^{-1}$; uv λmax (MeOH) 232 nm ($\epsilon$20,600). The product contained a small amount of ammonium chloride but was suitable for the next step, see example 3.

*Nujol is a trademark for a brand of white mineral oil

EXAMPLE 2

4,7-Dihydro-6-methoxy-4,7-dioxo-1H-cyclohepta[b]pyridine-3-carboxylic Acid (II; $R^7$=CH$_3$O and $R^8$=H)

5-Amino-2-methoxy-2,4,6-cycloheptatrien-1-one hydrochloride (13 g, 0.07 mole), described in example 1a, was added to a sodium ethoxide solution (prepared from 16.1 g, 0.07 gram atom, of sodium and 200 ml of anhydrous ethanol). After 20 min at 25° C., the reaction mixture was filtered. The filtrate was evaporated to dryness. Diethyl ethoxymethylenemalonate (50 ml) was added to the residue. The resulting solution was heated at 140° C. for 2 hr. Diethyl ether (500 ml) was added to the cooled reaction mixture. The precipitate was collected and purified by chromatography on silica gel using methylene chloride-acetone (9:1) as the eluent. The pure fractions were pooled to yield 16.6 g of 2-[(4-methoxy-5-oxo-1,3,6-cycloheptatrien-1-yl)aminomethylene]propanedioic acid diethyl ester (V; $R^7$=CH$_3$O and $R^8$=C$_2$H$_5$); mp 108°-110° C.; nmr (CDCl$_3$) δ1.35 (t, 6H), 3.9 (s, 3H), 4.35 (m, 4H), 7.0 (m, 4H), 8.35 (d, 1H), 11.0 (d, 1H).

A mixture of the latter compound (5 g) and diphenyl ether (100 ml) was heated at 250° C. for 40 min. The reaction mixture was cooled and the resulting precipitate was collected, washed with methanol and dried to give 3.7 g of 4,7-dihydro-6-methoxy-4,7-dioxo-1H-cyclohepta[b]pyridine-3-carboxylic acid ethyl ester (II: $R^7$=CH$_3$O and $R^8$=C$_2$H$_5$).

The latter ester (1.5 g) was heated at reflux for 2 hr with 35 ml of 15% (w/v) aqueous HCl. The precipitate was collected, washed with water and acetone and dried to give 1.13 g of the title compound; mp>280° C.; nmr (DMSO-d$_6$) δ3.4 (broad s, 2H), 3.9 (s, 3H), 7.15-8.7 (m, 4H); ir (Nujol*) 3450, 2800, 1710, 1555, 1155; uv λmax (EtOH) 344 nm ($\epsilon$10,860), 292 (14,620), shoulder at 263 (17, 570), 245 (29,730); Anal Calcd for C$_{12}$H$_9$NO$_5$: C, 58.30% H, 3.67% N, 5.67%; Found: C, 58,32% H, 3.54% N, 5.77%.

*Trademark

EXAMPLE 3

6-Benzyloxy-4,7-dihydro-4,7-dioxo-1H-cyclohepta[b]pyridine-3-carboxylic acid Ethyl Ester (II; $R^7$=OCH$_2$C$_6$H$_5$ and $R^8$=C$_2$H$_5$)

A mixture of 5-amino-2-benzyloxy-2,4,6-cycloheptatrien-1-one (10 g), described in example 1b, and diethyl ethoxymethylenemalonate (100 ml) was heated at 140° C. for 1.5 hr. The cooled reaction mixture was subjected to chromatography on silica gel using dichloromethane-acetone (9:1) as the eluant. The pure fractions were pooled to give 2-[(4-benzyloxy-5-oxo-1,3,6-cycloheptatrien-1-yl)aminomethylene]propanedioic acid diethyl ester (V; $R^7$=OCH$_2$C$_6$H$_5$ and $R^8$=C$_2$H$_5$); nmr (CDCl$_3$) δ1.3 (m 6H), 4.2 (m, 4H), 5.2 (s, 2H), 7.2 (m, 2H), 7.2 (m, 9H), 8.25 (d, 1H), 10.9 (d, 1H); ir (CHCl$_3$) 3490, 3240, 1700, 1690, 1570; uv λmax (MeOH) 279 nm ($\epsilon$10,410), 224 (27,380).

The latter compound (2 g) was added in one portion to boiling diphenyl ether (50 ml). The mixture was boiled for 10 minutes, cooled and subjected to chromatography on silica gel using chloroform-methanol (19:1) as the eluant. The appropriate fractions were pooled to give the title compound; nmr (DMSO-d$_6$) δ1.25 (t, 3H), 4.2 (q, 2H), 5.15 (s, 2H), 7.35 (m, 7h), 8.05 (s, 1H), 8.35 (s, 1H); ir (Nujol*) 3000, 1710, 1620, 1560 cm$^{-1}$; uv λmax (EtOH) 353 nm (ε12,760), 304 (11,105), 246 (30,115).

*Trademark

EXAMPLE 4

4,7-Dihydro-6-hydroxy-4,7-dioxo-1H-cyclohepta[b]pyridine-1-carboxylic Acid Ethyl Ester (II; R$^7$=OH and R$^8$=C$_2$H$_5$)

A mixture of 5-amino-6-hydroxy-2,4,6-cycloheptatrien-1-one (5.76 g), described by T. Nozoe et al., Proc. Japan Acad., 27, 188 (1951), and diethyl ethoxymethylenemalonate (15.2 g) was heated at 140° C. for 2 hr. The reaction mixture was cooled and dissolved in ethanol. The resulting crystalline precipitate was collected, treated with charcoal in a chloroform solution and the recrystallized from ethanol to give 4.76 g of 2-[(4-hydroxy-5-oxo-1,3,6-cycloheptatriene-1-yl)aminomethylene]propanedioic acid (V; R$^7$=OH and R$^8$=C$_2$H$_5$), mp 175°-176° C.

A mixture of the latter compound (7.76 g) and diphenyl ether (176 ml) was heated at reflux for 25 minutes. The mixture was cooled to 25° C. and diluted with hexane. The resulting precipitate was collected and washed with hexane to give 6.38 g of the title compound, mp>260° C.

Hydrolysis of the latter compound with 19% aqueous HCl at 100° C. for 45 min gave the corresponding acid, 1,4-dihydro-6-hydroxy-4,7-dioxo-1H-cyclohepta[b]pyridine-1-carboxylic acid; mp>290° C.; Anal Calcd for C$_{11}$H$_7$NO$_5$: C, 56.66% H, 3.03% N, 6.01%; Found: C, 56.46% H, 3.06% N, 5.96%.

EXAMPLE 5

3-(Ethoxycarbonyl)-4,7-dihydro-6-methoxy-4,7-dioxo-1H-cyclohepta[b]pyridine-1-acetic Acid Ethyl Ester (I; R$^1$=CH$_2$COOC$_2$H$_5$; R$^2$=COOC$_2$H$_5$ and R$^3$=OCH$_3$)

A mixture of 4,7-Dihydro-6-methoxy-4,7-dioxo-1H-cyclohepta[b]pyridine-3-carboxylic acid ethyl ester (2 g), described in example 2, DMF (20 ml) and sodium hydride (400 mg, 50% suspension in mineral oil) was stirred at 25° C. for 30 min. Ethyl bromoacetate (2 g) was added to the mixture and the mixture was heated at 100°-105° C. for 15 hr. The cooled mixture was filtered and the filtrate was poured onto a mixture of ice and water. The resulting mixture was extracted with chloroform. The residue, obtained by evaporation of the chloroform extract, was purified by chromatography on silica gel using chloroform-methanol (49:1) as the eluant. Pooling of the appropriate fractions gave 1.1 g of the title compound; mp 216°-218° C.; nmr (CDCl$_3$) δ1.35 (t, 6H), 4.05 (s, 3H), 4.35 (m, 4H), 4.95 (s, 2H), 7.2 (m, 2H), 8.3 (s, 2H).

In the same manner, but replacing 4,7-dihydro-6-methoxy-4,7-dioxo-1H-cyclohepta[b]pyridine-3-carboxylic acid ethyl ester with an equivalent amount of 4,7-dihydro-6-hydroxy-4,7-dioxo-1H-cyclohepta[b]pyridine-1-carboxylic acid ethyl ester, described in example 4, and changing the reaction time and temperature to 3 days at 25° C. following the addition of the ethyl bromoacetate, 3-(ethoxycarbonyl)-6-[(2-ethoxy-2-oxoethyl)oxy]-4,7-dihydro-4,7-dioxo-1H-cyclohepta[b]pyridine-1-acetic acid ethyl ester (I; R$^1$=CH$_2$COOC$_2$H$_5$, R$^2$=COOC$_2$H$_5$ and R$^3$=OCH$_2$COOC$_2$H$_5$, mp 115°-116° C., nmr (CDCl$_3$) δ1.35 (m, 9H), 4.30 (m, 6H), 4.87 (s, 2H), 5.00 (s, 2H), 7.15-8.2 (m, 4H), was obtained.

EXAMPLE 6

6-Benzyloxy-3-(ethoxycarbonyl)-4,7-dihydro-4,7-dioxo-1H-cyclohepta[b]pyridine-1-acetic Acid Ethyl Ester (I; R$^1$=CH$_2$COOC$_2$H$_5$, R$^2$=COOC$_2$H$_5$ and R$^3$=OCH$_2$C$_6$H$_5$)

A mixture of 6-benzyloxy-4,7-dihydro-4,7-dioxo-1H-cyclohepta[b]pyridine-3-carboxylic acid ethyl ester (1.7 g), described in example 4, ethyl bromoacetate (2 g), potassium carbonate (2 g) and DMF (50 ml) was stirred at 25° C. for 3 hr. The reaction mixture was diluted with water and extracted with chloroform. The residue, obtained by evaporation of the chloroform extract, was purified by chromatography on silica gel using chloroform-methanol (49:1) as the eluant. The appropriate fractions were pooled to give 0.9 g of the title compound, nmr (CDCl$_3$) δ1.3 (m, 6H), 4.35 (m, 4H), 4.8 (s, 2H), 5.3 (s, 2H), 7.3 (m, 7H), 8.2 (s, 1H), 8.35 (s, 1H).

EXAMPLE 7

3-Carboxy-4,7-dihydro-6-methoxy-4,7-dioxo-1H-cyclohepta[b]pyridine-1-acetic Acid (I; R$^1$=CH$_2$COOH, R$^2$=COOH and R$^3$=OCH$_3$)

3-(Ethoxycarbonyl)-4,7-dihydro-6-methoxy-4,7-dioxo-1H-cyclohepta[b]pyridine-1-acetic acid ethyl ester (2.5 g), described in example 5, was heated at reflux in 15% (w/v) aqueous HCl for 2 hr. The resulting precipitate was collected, washed with water and acetone, and recrystallized from water to give 1.8 g of the title compound; mp 272°-274° C.; nmr (DMSO-d$_6$) δ3.95 (s, 3H), 5.5 (s, 2H), 7.28 & 7.75 (2d, 2H), 7.95 (s, 1H), 9.0 (1H, s); ir (Nujol*) 2900, 1700, 1565, 1265, 1165 cm$^{-1}$; uv λmax (MeOH) 347 nm (ε11,630), 306 (10,470), 266 (21,365), 249 (32,290). An analytical sample dried under reduced pressure at 140° C. was hygroscopic; Anal Calcd for C$_{14}$H$_{11}$NO$_7$: C, 55.09% H, 3.63% N, 4.59%; Found: C, 54.41% H, 3.60% N, 4.55%.

In the same manner but replacing 3-(ethoxycarbonyl)-4,7-dihydro-6-methoxy-4,7-dioxo-1H-cyclohepta[b]pyridine-1-acetic acid ethyl ester with an equivalent amount of 3-(ethoxycarbonyl)-6-[(2-ethoxy-2-oxoethyl)oxy]-4,7-dihydro-4,7-dioxo-1H-cyclohepta[b]pyridine-1-acetic acid ethyl ester, described in example 5, 3-carboxy-6-[(carboxymethyl)oxy]-4,7-dihydro-4,7-dioxo-1H-cyclohepta[b]pyridine-1-acetic acid monohydrate (R$^1$=CH$_2$COOH, R$^2$=COOH and R$^3$=OCH$_2$COOH); mp 245°-246° C.; nmr (DMSO-d$_6$) δ4.95 (s, 2H), 5.55 (s, 2H), 7.3-7.8 (d, J=13 Hz, 4H), 9.03 (s, 1H); ir (Nujol*) 2900, 1764, 1714, 1675 cm$^{-1}$; uv λmax (MeOH) 344 nm (ε12,570), 305 (11,000), 265 (20,920), 4.29 (30,170); Anal Calcd for C$_{15}$H$_{11}$NO$_9$.H$_2$O: C, 49.06% H, 3.57% N, 3.81%; Found: C, 49.01% H, 3.53% N, 3.80%; was obtained.

EXAMPLE 8

6-Benzyloxy-3-carboxy-4,7-dihydro-4,7-dioxo-1H-cyclohepta[b]pyridine-1-acetic Acid (I; R$^1$=CH$_2$COOH, R$^2$=COOH and R$^3$=OCH$_2$C$_6$H$_5$)

A suspension of 6-benzyloxy-3-(ethoxycarbonyl)-4,7-dihydro-4,7-dioxo-1H-cyclohepta[b]pyridine-1-acetic acid ethyl ester (437 mg), described in example 6, in 2% (w/v) aqueous NaOH (5 ml) and ethanol (5 ml) was stirred at 25° C. for one hr. The suspension was diluted with water, rendered acidic by the addition of concentrated HCl and extracted with chloroform. The residue, obtained after evaporation of the chloroform extract, was crystallized from acetone-water to give 350 mg of the title compound as a monohydrate; mp>250° C.; nmr (DMSO-d$_6$) δ5.25 (s, 2H), 5.5 (s, 2H), 7.4 (m, 8H), 9.0 (s, 1H), ir (Nujol*) 3450, 2900, 1725, 1570 cm$^{-1}$; uv λmax (MeOH) 347 nm (ε9,270), 301 (10,105), 263 (19,250), 249 (24,165); Anal Calcd for C$_{20}$H$_{15}$NO$_7$.H$_2$O: C, 60.15% H, 4.29% N, 3.51%; Found: C, 60.14% H, 4.34% N, 3.50%.

*Trademark

We claim:

1. A compound of formula 1

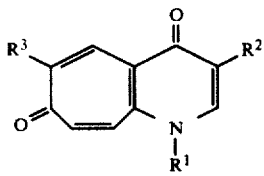

in which R$^1$ is CH$_2$COOR$^4$ wherein R$^4$ is hydrogen or lower alkyl; R$^2$ is COOR$^5$ wherein R$^5$ is hydrogen or lower alkyl; and R$^3$ is lower alkoxy, benzyloxy or OCH$_2$COOR$^6$ wherein R$^6$ is hydrogen or lower alkyl; with the provisos that when R$^4$ is hydrogen then R$^5$ and R$^6$ is hydrogen, and that when R$^4$ is lower alkyl then R$^5$ and R$^6$ are lower alkyl with R$^4$ and R$^6$ being the same lower alkyl; or a therapeutically acceptable salt, with an organic or inorganic base, of the compound of formula I having carboxyls.

2. The compound of formula I, as claimed in claim 1, wherein R$^1$ is CH$_2$COOR$^4$ wherein R$^4$ is hydrogen, methyl or ethyl; R$^2$ is COOR$^5$ wherein R$^5$ is hydrogen, methyl or ethyl; and R$^3$ is methoxy, benzyloxy or OCH$_2$COOR$^6$ wherein R$^6$ is hydrogen, methyl or ethyl.

3. The compound of formula I, as claimed in claim 1, wherein R$^1$ is CH$_2$COOH, R$^2$ is COOH and R$^3$ is methoxy, benzyloxy or OCH$_2$COOH.

4. 3-(Ethoxycarbonyl)-4,7-dihydro-6-methoxy-4,7-dioxo-1H-cyclohepta[b]pyridine-1-acetic acid ethyl ester, as claimed in claim 1.

5. 3-(Ethoxycarbonyl)-6-[(2-ethoxy-2-oxoethyl)oxy]-4,7-dihydro-4,7-dioxo-1H-cyclohepta[b]pyridine-1-acetic acid ethyl ester, as claimed in claim 1.

6. 6-Benzyloxy-3-(ethoxycarbonyl)-4,7-dihydro-4,7-dioxo-1H-cyclohepta[b]pyridine-1-acetic acid ethyl ester, as claimed in claim 1.

7. 3-Carboxy-4,7-dihydro-6-methoxy-4,7-dioxo-1H-cyclohepta[b]pyridine-1-acetic acid, as claimed in claim 1.

8. 3-Carboxy-6-[(carboxymethyl)oxy]-4,7-dihydro-4,7-dioxo-1H-cyclohepta[b]pyridine-1-acetic acid, as claimed in claim 1.

9. 6-Benzyloxy-3-carboxy-4,7-dihydro-4,7-dioxo-1H-cyclohepta[b]pyridine-1-acetic acid, as claimed in claim 1.

10. A pharmaceutical composition for preventing or relieving diabetic complications, selected from neuropathy, nephropathy, retinopathy and cataracts, in a diabetic mammal, which comprises a therapeutically effective amount of a compound of claim 1, or a therapeutically acceptable salt thereof with an organic or inorganic base, and a pharmaceutically acceptable carrier.

11. A method of preventing or relieving a diabetic complication selected from neuropathy, nephropathy, retinopathy and cataracts, in a diabetic mammal, which comprises administering to said mammal an alleviating or prophylactic amount of a composition of claim 10.

* * * * *